(12) United States Patent
Fisch

(10) Patent No.: US 6,391,920 B1
(45) Date of Patent: May 21, 2002

(54) METHODS OF TREATING ANDROGEN DEFICIENCY IN MEN USING SELECTIVE ANTIESTROGENS

(76) Inventor: Harry Fisch, 30 Springdale Rd., Scarsdale, NY (US) 10583

( * ) Notice: Subject to any disclaimer, the term of this patent is extended or adjusted under 35 U.S.C. 154(b) by 0 days.

(21) Appl. No.: 09/980,652
(22) PCT Filed: May 15, 2001
(86) PCT No.: PCT/US01/15900
§ 371 Date: Oct. 26, 2001
§ 102(e) Date: Oct. 26, 2001
(87) PCT Pub. No.: WO01/91744
PCT Pub. Date: Dec. 6, 2001

Related U.S. Application Data
(60) Provisional application No. 60/207,496, filed on May 26, 2000.

(51) Int. Cl.$^7$ ..................... A61K 31/225; A61K 31/135
(52) U.S. Cl. ........................................ 514/648; 514/651
(58) Field of Search ................................ 514/648, 651

(56) References Cited

U.S. PATENT DOCUMENTS

| | | |
|---|---|---|
| 5,728,688 A | 3/1998 | Labrie ........................ 514/178 |
| 5,861,389 A | 1/1999 | Radlmaier et al. .......... 514/177 |

OTHER PUBLICATIONS

Guay et al. "Male Counterpart to Hypothalamic Amenorrhea?" Urology, vol. XXXVIII, No. 4, pp. 317–322. Oct. 1991.

Cooper et al. "The Effects of Clomiphene in Impotence". Journal, I20, pp. 327–330. Nov. 1971.

Guay et al. "Effect of Raising Endogenous Testosterone Levels in Impotent Men with Secondary Hypogonadism: Double Blind Placebo–Controlled Trial with Clomiphene Citrate". Journal of Clinical Endocrinology and Metabolism, vol. 80, No. 12, pp. 3546–3552. 1995.

Fuse et al. "Changes in Seminal Plasma Transferrin Concentration following Administration of Clomiphene Citrate". Archives of Andrology:31, pp. 139–145. 1993.

Jarow. "Nonsurgical Treatment of male Infertility: Empiric Therapy." Therapy. pp. 410–422 (date of Publication Not Available).

International Search Report dated Nov. 5, 2001 for PCT/US01/15900.

*Primary Examiner*—Raymond Henley, III
(74) *Attorney, Agent, or Firm*—Ira J. Schaefer; Clifford Chance Rogers & Wells LLP

(57) ABSTRACT

Male menopause is characterized by significant decreases in serum levels of bioavailable androgens. The administration of antiestrogens to men experiencing male menopause can remedy the relative androgen deficiency in men by stimulating the body's production of testosterone.

14 Claims, No Drawings

METHODS OF TREATING ANDROGEN DEFICIENCY IN MEN USING SELECTIVE ANTIESTROGENS

This is a 371 of PCT/US01/15900 filed May 15, 2001 which claims the benefit of U.S. Provisional Application No. 60/207,496 filed May 26, 2000.

BACKGROUND OF THE INVENTION

The invention relates to the new use of antiestrogens for the production of a pharmaceutical agent for treating a relative androgen deficiency in men.

In men, increasing age leads to a reduction of testicular androgen production and androgen concentration in the organism. In contrast to the situation in women, in whom estrogen production drops to castration values within a comparatively short period, this takes decades in men and involves a gradual drop. The total concentration of testosterone in the serum in the older age group is significantly reduced compared to the values in young men. Because of the increase in steroid hormone-binding globulin (SHBG) that coincides with the aging process, moreover, the proportion of free, unbound, and thus biologically active testosterone drops. In addition, the serum levels of estrogens, although they are produced from androgens by direct conversion, do not drop in the same way as a function of age. As a result, the hormonal environment is significantly altered.

In men, the hormonal environment of the sexual steroids is characterized by a significant preponderance of androgens over estrogens. While the circulating main component of androgens, testosterone, is detected in the serum in units in the range of nmol/l, the estrogen antagonist, estradiol, can be measured only in the range of pmol/l. This considerable preponderance of androgen can be detected basically in the entire late puberty period of life, but there is a clearly different intensity of this androgen dominance as a function of age. With increasing age and particularly so in those over the age of 60, there is a less pronounced emphasis of the androgen preponderance.

In older men there are relative decreases in the preponderance of testosterone by 30–50% compared to the previous values found in young men.

The relative testosterone deficiency per se can be regarded as responsible for a number of age-related disorders. Reduction of muscle mass accompanied by limitation of body performance capacity, reduction of bone density and in individual cases even osteoporosis, an increase in prostate size referred to as benign prostatic hyperplasia, reduction of libido and potency, and psycho-vegetative disorders such as depression, which are disorders that are often generically referred to as Male Menopause and are caused by relative androgen deficiency in men. Libido is the desire to obtain an erection, while potency is the ability to have that erection.

It is known that in younger men, testosterone values are also effectively increased by daily treatment with antiestrogens to treat male infertility. Treatment of Male Infertility, Springer-Verlag Berlin, Heidelberg, New York 1982; Fuse, H. et al., Archives of Andrology 31 (1993) 139–145); Nonsurgical Treatment of Male Infertility, Jarow, J., Infertility in the Male, pp. 410–422. However, it has been thought that antiestrogens do not seem well suited for treatment of a relative androgen deficiency in men. Thus, for example, U.S. Pat. No. 5,861,389 proposes the use of at least one aromatase inhibitor for the production of a pharmaceutical agent for treating a relative androgen deficiency in men.

SUMMARY OF THE INVENTION

The object of the present invention is to treat a relative androgen deficiency in older men and/or the specific disorders related to male menopause by the use of antiestrogens.

It has been noted that the use of antiestrogens in treating a relative androgen deficiency in older men results surprisingly in a long-term increase in the androgen level.

By gradually stimulating the body to produce testosterone, the antiestrogens result in an endogenic rebalancing of the testosterone/estrogen ratio in men. As a result, the relative androgen deficiency is compensated for.

For the purposes of this invention, antiestrogens are all those compounds that compete with estrogen for estrogen-receptor-binding sites and may delay replenishment of intracellular estrogen receptors. As antiestrogens, therefore, all such compounds are suitable, such as, for example:

tamoxifen citrate which is the trans-isomer of a triphenylethylene derivative. The chemical name is (Z)2-[4-(1,2-diphenyl-1-butenyl) phenoxy]-N,N-dimethylethanamine 2-hydroxy-1,2,3-propanetricarboxylate (1:1) and sold under the trademark Novladex; and clomiphene citrate which is 2[p-(2-chloro-1,2-diphenylvinyl) phenoxy]] triethlamine citrate (1:1). It has the molecular formula of $C_{26}H_{28}ClNO \cdot C_6H_8O_7$ and a molecular weight of 598.09 and is sold under the trademark Clomid.

The list of antiestrogens above is not exhaustive, other compounds that meet the set requirements, are also considered.

A pharmaceutically effective dosage of the antiestrogen is administered in older men for an effective time period, preferably continuously. For example, at a daily dose of 5–10 mg once or twice a day, tamoxifen is administered to obtain a target range of mid-normal testosterone levels. A dose of 10–25 mg of clomid daily or every other day and up to 100 mg is administered to obtain the mid-normal levels. Measuring the serum concentration of testosterone and estradiol can thus give early indication of whether the desired hormone balance was achieved and optionally whether dose adjustment can be undertaken.

In general, 5 to 1000 mg, preferably 10 to 100 mg, of antiestrogen clomiphene citrate or tamoxifen citrate or a biologically equieffective amount of another antiestrogen is used daily or every other day to treat a relative androgen deficiency in men.

The antiestrogens can be administered, e.g., orally, parenterally or transdermally by a patch for example.

For the preferred oral administration, suitable means are especially tablets, coated tablets, capsules, pills, suspensions, or solutions that can be produced in a way that is commonly used and familiar to one skilled in the art, with the additives and vehicles that are commonly used for the formulation of antiestrogens that are to be administered orally.

The pharmaceutical agent that is produced according to the invention contains as an active ingredient per dosage unit of the antiestrogen at a daily or every other day dosage of 5 to 100 mg in addition to the commonly used additives, vehicles and/or diluents or other antiestrogens at biologically equieffective dosages.

When antiestrogens are used for treating male menopause, the estrogen concentration is effectively lowered. The easy controllability of the treatment distinguishes treatment with an antiestrogen. For 10 mg tablets, each tablet contains 15.2 mg of tamoxifen citrate which is equivalent to 10 mg of tamoxifen. For 20 mg tablets, each tablet contains 30.4 mg of tamoxifen citrate which is equivalent to 20 mg of tamoxifen. The inactive ingredients are carboxymethylcellulose calcium, magnesium stearate, mannitol and starch.

Clomiphene citrate tablets is a mixture of two geometric isomers [cis (zuclomiphene) and trans (enclomiphene)] containing between 30% and 50% of the cis-isomer. A standard commercially available tablet contains 50 mg clomiphene citrate and the following inactive ingredients: corn starch, lactose, magnesium stearate, pregelatinized corn starch, and sucrose. The current tablets are used primarily for treating female infertility. Treatment according to the present invention contemplates a redosing to accommodate the lower dosages specified herein.

It is also contemplated that combinations of antiestrogens can be administered or that combinations of antiestrogens and other testosterone producing drugs can be used.

What is claimed is:

1. A method of treating androgen deficiency in men comprising administering a selective antiestrogen.

2. The method according to claim 1, wherein the selective antiestrogen is clomiphene.

3. The method according to claim 1, wherein the selective antiestrogen is clomiphene citrate.

4. A method of treating disorders related to male menopause in men comprising administering an antiestrogen.

5. The method according to claim 4, wherein the disorder is reduction of muscle mass.

6. The method according to claim 4, wherein the disorder is limitation of body performance capacity.

7. The method according to claim 4, wherein the disorder is reduction of bone density.

8. The method according to claim 4, wherein the disorder is reduction of libido.

9. The method according to claim 4, wherein the disorder is reduction of potency.

10. The method according to claim 4, wherein the disorder is reduction of benign prostatic hyperplasia.

11. The method according to claim 1, wherein the selective antiestrogen is tamoxifen.

12. The method according to claim 1, wherein the selective antiestrogen is tamoxifen citrate.

13. The method according to claim 3, wherein the clomiphene citrate comprises the cis-isomer.

14. The method according to claim 3, wherein the clomiphene citrate comprises the trans-isomer.

* * * * *

(12) EX PARTE REEXAMINATION CERTIFICATE (5338th)
United States Patent
Fisch

(10) Number: US 6,391,920 C1
(45) Certificate Issued: Apr. 11, 2006

(54) METHODS OF TREATING ANDROGEN DEFICIENCY IN MEN USING SELECTIVE ANTIESTROGENS

(75) Inventor: Harry Fisch, 30 Springdale Rd., Scarsdale, NY (US) 10583

(73) Assignee: Harry Fisch, Scarsdale, NY (US)

Reexamination Request:
No. 90/006,921, Jan. 26, 2004

Reexamination Certificate for:
| | |
|---|---|
| Patent No.: | 6,391,920 |
| Issued: | May 21, 2002 |
| Appl. No.: | 09/980,652 |
| Filed: | Oct. 26, 2001 |

(22) PCT Filed: May 15, 2001
(86) PCT No.: PCT/US01/15900
§ 371 (c)(1),
(2), (4) Date: Oct. 26, 2001
(87) PCT Pub. No.: WO01/91744
PCT Pub. Date: Dec. 6, 2001

Related U.S. Application Data
(60) Provisional application No. 60/207,496, filed on May 26, 2000.

(51) Int. Cl.
*A61K 31/138* (2006.01)

(52) U.S. Cl. ........................ 514/648; 514/651
(58) Field of Classification Search .............. 514/648, 514/651
See application file for complete search history.

(56) References Cited

U.S. PATENT DOCUMENTS

2004/0097597 A1  5/2004  Podolski et al. ............ 514/651

OTHER PUBLICATIONS

A. Guay et al., Inter. J. Impotence Res., 15: 156–165 (2003).

Guay et al., "Results of Double Blinded Treatment With Clomiphene Citrate In Patients With Hypogonadotropic Hypogonadism," Annual Meeting of the Endocrine Society, Abstract No. 386, Jun. 1993.

Morales et al., "Andropause: a misnomer for a true clinical entity," J Urol., vol. 163, No. 3, pp. 705–712, Mar. 2000, Abstract.

Sternbach H., "Age–associated testosterone decline in men: clinical issues for psychiatry," Am J Psychiatry, vol. 155, No. 10, pp. 1310–1318, 1998, Abstract.

Suzuki et al., "Endocrine environment of benign prostatic hyperplasia: prostate size and volume are correlated with serum estrogen concentration," Scand J Urol Nephrol., vol. 29, No. 1, pp. 65–68, 1995, Abstract.

Guay et al., "Male Counterpart to Hypothalamic Amenorrhea?" Urology, vol. XXXVIII, No. 4, pp. 317–322, 1991.

Guay et al., "Effect of Raising Endogenous Testosterone Levels in Impotent Men with Secondary Hypogonadism: Double Blind Placebo–Controlled Trial with Clomiphene Citrate," Journal of Clinical Endocrinology and Metabolism, vol. 80, No. 12, pp. 3546–3552, 1995.

Jarow, "Nonsurgical Treatment of Male Infertility: Empiric Therapy," pp. 410–422, 1996.

*Primary Examiner*—Phyllis G. Spivack

(57) ABSTRACT

Male menopause is characterized by significant decreases in serum levels of bioavailable androgens. The administration of antiestrogens to men experiencing male menopause can remedy the relative androgen deficiency in men by stimulating the body's production of testosterone.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 4 are determined to be patentable as amended.

Claims 2, 3 and 5–14, dependent on an amended claim, are determined to be patentable.

New claims 15–20 are added and determined to be patentable.

1. A method of treating *disorders related to* androgen deficiency in men comprising administering a selective antiestrogen *to men in need of such treating*.

4. A method of treating disorders related to male menopause in men comprising administering an antiestrogen *to men in need of such treating*.

*15. The method according to claim 4, wherein the antiestrogen is clomiphene.*

*16. The method according to claim 4, wherein the antiestrogen is clomiphene citrate.*

*17. The method according to claim 16, wherein the clomiphene citrate comprises the cis-isomer.*

*18. The method according to claim 16, wherein the clomiphene citrate comprises the trans-isomer.*

*19. The method according to claim 4, wherein the antiestrogen is tamoxifen.*

*20. The method according to claim 4, wherein the antiestrogen is tamoxifen citrate.*

* * * * *

(12) EX PARTE REEXAMINATION CERTIFICATE (9617th)
United States Patent
Fisch

(10) Number: US 6,391,920 C2
(45) Certificate Issued: Apr. 29, 2013

(54) METHODS OF TREATING ANDROGEN DEFICIENCY IN MEN USING SELECTIVE ANTIESTROGENS

(76) Inventor: Harry Fisch, Scarsdale, NY (US)

Reexamination Request:
No. 90/008,024, May 1, 2006

Reexamination Certificate for:
Patent No.: 6,391,920
Issued: May 21, 2002
Appl. No.: 09/980,652
Filed: Oct. 26, 2001

Reexamination Certificate C1 6,391,920 issued Apr. 11, 2006

(21) Appl. No.: 90/008,024
(22) PCT Filed: May 15, 2001
(86) PCT No.: PCT/US01/15900
§ 371 (c)(1), (2), (4) Date: Oct. 26, 2001
(87) PCT Pub. No.: WO01/91744
PCT Pub. Date: Dec. 6, 2001

Related U.S. Application Data

(60) Provisional application No. 60/207,496, filed on May 26, 2000.

(51) Int. Cl.
*A61K 31/138* (2006.01)
*A61K 31/135* (2006.01)
*A61K 31/225* (2006.01)
*A61K 31/21* (2006.01)

(52) U.S. Cl.
USPC ............................................ 514/648; 514/651

(58) Field of Classification Search ....................... None
See application file for complete search history.

(56) References Cited

To view the complete listing of prior art documents cited during the proceeding for Reexamination Control Number 90/008,024, please refer to the USPTO's public Patent Application Information Retrieval (PAIR) system under the Display References tab.

*Primary Examiner* — Shri Ponnaluri

(57) ABSTRACT

Male menopause is characterized by significant decreases in serum levels of bioavailable androgens. The administration of antiestrogens to men experiencing male menopause can remedy the relative androgen deficiency in men by stimulating the body's production of testosterone.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2-3 and 11-20 is confirmed.

Claims 1 and 4-9 are cancelled.

Claim 10 is determined to be patentable as amended.

10. The method according to claim 4, wherein the disorder is [reduction of] benign prostatic hyperplasia.

\* \* \* \* \*